(12) United States Patent
Hauser et al.

(10) Patent No.: US 9,504,570 B2
(45) Date of Patent: Nov. 29, 2016

(54) DEVICE AND METHOD FOR RESHAPING TRICUSPID VALVE ANNULUS

(71) Applicant: Edwards Lifesciences Corporation, Irvine, CA (US)

(72) Inventors: David L. Hauser, Newport Beach, CA (US); Donald E. Bobo, Jr., Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 369 days.

(21) Appl. No.: 14/159,251

(22) Filed: Jan. 20, 2014

(65) Prior Publication Data
US 2014/0135910 A1    May 15, 2014

Related U.S. Application Data

(63) Continuation of application No. 13/453,906, filed on Apr. 23, 2012, now abandoned, which is a continuation of application No. 12/891,522, filed on Sep. 27, 2010, now abandoned, which is a continuation of application No. 12/324,293, filed on Nov. 26, 2008, now Pat. No. 7,803,187, which is a continuation of application No. 11/519,645, filed on Sep. 11, 2006, now abandoned.

(60) Provisional application No. 60/716,012, filed on Sep. 9, 2005.

(51) Int. Cl.
*A61F 2/82*    (2013.01)
*A61F 2/24*    (2006.01)
*A61F 2/848*    (2013.01)

(52) U.S. Cl.
CPC .......... *A61F 2/2454* (2013.01); *A61F 2/2445* (2013.01); *A61F 2/82* (2013.01); *A61F 2/246* (2013.01); *A61F 2/2442* (2013.01); *A61F 2/2478* (2013.01); *A61F 2/2487* (2013.01); *A61F 2002/8483* (2013.01); *A61F 2210/0004* (2013.01); *A61F 2210/0014* (2013.01); *A61F 2220/0016* (2013.01); *A61F 2230/0004* (2013.01)

(58) Field of Classification Search
CPC .................................... A61F 2/2487–2002/249
See application file for complete search history.

(56) References Cited

U.S. PATENT DOCUMENTS

| | | | | |
|---|---|---|---|---|
| 7,018,406 | B2 * | 3/2006 | Seguin ................. | A61F 2/2418 606/194 |
| 2005/0075662 | A1 * | 4/2005 | Pedersen ............... | A61B 17/22 606/194 |
| 2005/0197694 | A1 * | 9/2005 | Pai .................. | A61B 17/00234 623/2.1 |
| 2014/0379006 | A1 * | 12/2014 | Sutherland ........... | A61F 2/2487 606/151 |

* cited by examiner

*Primary Examiner* — Yashita Sharma
*Assistant Examiner* — Rebecca Preston

(57) ABSTRACT

A device for reshaping the tricuspid valve comprises a stent that is deployed in the right ventricular outflow tract (RVOT) adjacent to the tricuspid valve and expanded to a size sufficient to reduce the annular diameter or size of the tricuspid valve, thereby improving coaptation of the leaflets and reducing regurgitation. Embodiments of the device are deliverable percutaneously.

13 Claims, 16 Drawing Sheets

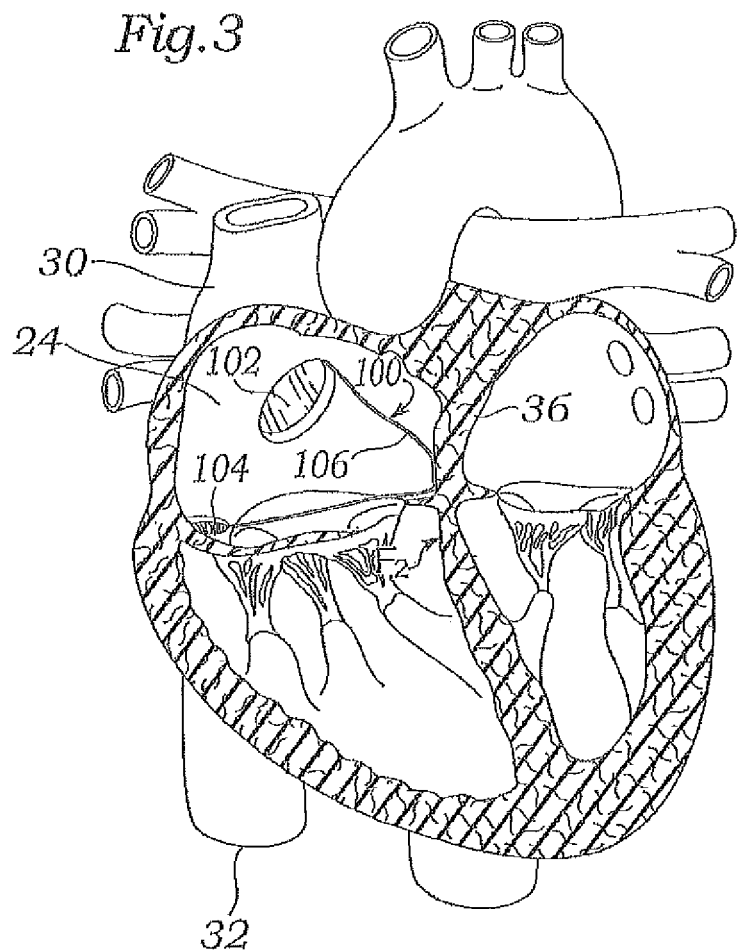

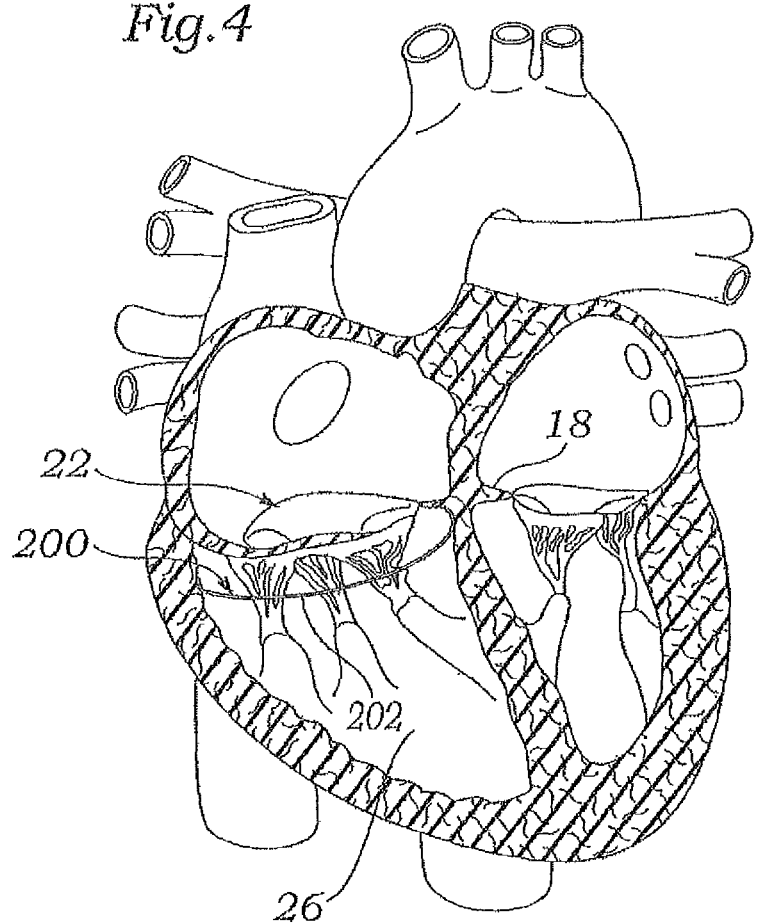

DEVICE AND METHOD FOR RESHAPING TRICUSPID VALVE ANNULUS

CROSS REFERENCE TO RELATED APPLICATIONS

This application is a continuation of U.S. patent application Ser. No. 13/453,906, filed Apr. 23, 2012, which is a continuation of U.S. patent application Ser. No. 12/891,522, filed Sep. 27, 2010, which is a continuation of U.S. patent application Ser. No. 12/324,293, filed Nov. 26, 2008, now U.S. Pat. No. 7,803,187, which is a continuation of U.S. patent application Ser. No. 11/519,645, filed Sep. 11, 2006, which claims the benefit of U.S. Patent Application No. 60/716,012, filed on Sep. 9, 2005, the entire disclosures of which are incorporated by reference.

FIELD OF THE INVENTION

The present invention relates to medical devices and methods and, more particularly, to medical devices and methods for repairing a defective mitral valve in a human heart.

BACKGROUND

Heart valve regurgitation, or leakage from the outflow to the inflow side of a heart valve, occurs when a heart valve fails to close properly. Regurgitation often occurs in the mitral valve, located between the left atrium and left ventricle, or in the tricuspid valve, located between the right atrium and right ventricle. Regurgitation through the mitral valve is typically caused by changes in the geometric configurations of the left ventricle, papillary muscles and mitral valve annulus. Similarly, regurgitation through the tricuspid valve is typically caused by changes in the geometric configurations of the right ventricle, papillary muscles and tricuspid valve annulus. These geometric alterations result in incomplete leaflet coaptation during ventricular systole, thereby producing regurgitation.

A variety of heart valve repair procedures have been proposed over the years for treating heart valve regurgitation. With the use of current surgical techniques, it has been found that between 40% and 60% of regurgitant heart valves can be repaired, depending on the surgeon's experience and the anatomic conditions present. The advantages of heart valve repair over heart valve replacement are well documented. These advantages include better preservation of cardiac function and reduced risk of anticoagulant-related hemorrhage, thromboembolism and endocarditis. Although surgical techniques are typically effective for treating heart valve regurgitation, due to age or health considerations, many patients cannot withstand the trauma associated with an open-heart surgical procedure.

In recent years, a variety of new minimally invasive procedures for repairing heart valves have been introduced. These minimally invasive procedures do not require opening the chest or the use of cardiopulmonary by-pass. At least one of these procedures involves introducing an implant into the coronary sinus for remodeling the mitral annulus. The coronary sinus is a blood vessel commencing at the coronary sinus ostium in the right atrium and passing through the atrioventricular groove in close proximity to the posterior, lateral and medial aspects of the mitral annulus. Because the coronary sinus is positioned adjacent to the mitral valve annulus, an implant deployed within the coronary sinus may be used to apply a compressive force along a posterior portion of the mitral annulus for improving leaflet coaption.

Although implants configured for use in the coronary sinus have shown promising results, it has been found that this treatment may not be effective for all patients. For example, in certain cases, the coronary sinus may be too weakened or fragile to support the implant. In other cases, due to variations in heart anatomy, the location of the coronary sinus may not be well-situated for treating the mitral valve. For example, the coronary sinus may be above or below the mitral valve annulus, thereby diminishing the effectiveness of the implant. In other cases, it has been found that deployment of the implant in the coronary sinus may impinge on the circumflex artery. Due to the limitations associated with existing treatment procedures, a need exists for still further approaches for treating heart valve regurgitation in a minimally invasive manner.

SUMMARY OF THE INVENTION

Preferred embodiments of the present invention provide new devices and methods for treating heart valve regurgitation. The devices and methods are particularly well suited for treating mitral valve regurgitation in a minimally invasive manner.

In one preferred embodiment, an implantable body is configured for deployment in the right atrium. The body is shaped to apply a lateral force along the atrial septum at a location adjacent to the mitral valve. The force causes the atrial septum to deform, thereby affecting the anatomy on the left side of the heart. More particularly, by pressing on the atrial septum, the anterior leaflet of the mitral valve is pushed toward the posterior leaflet. The amount of force can be selected such that the anterior leaflet is pushed a sufficient amount for closing the gap in the mitral valve and reducing or eliminating mitral valve regurgitation.

One preferred device configured for this purpose generally comprises at least one anchor member for anchoring the device relative to the right atrium and a pusher member for engaging and pressing against the atrial septum. The anchor member may comprise an expandable stent configured for deployment in the superior vena cava. If desired, the anchor member may further comprise a second expandable stent configured for deployment in the inferior vena cava. The pusher member is coupled to the first and second anchors. The pusher member may comprise a bow-shaped member.

In another preferred embodiment, a device is provided for placement in the right ventricle. In one aspect, the device comprises a ring or U-shaped member that changes shape for pushing against the ventricular septum.

In another preferred embodiment, an expandable stent is configured for deployment in the left ventricular outflow tract. The expandable stent is adapted to exert a radial force for reshaping a mitral valve annulus, thereby moving an anterior leaflet of a mitral valve in a posterior direction. The device is preferably deployed at a location adjacent the aortic valve and, more preferably, the device is deployed beneath the aortic valve. The stent may be configured with a protrusion to increase the force applied along the portion of the LVOT that is adjacent to the mitral valve. The stent may further comprise a valvular structure to provide a prosthetic valve configured for replacing an aortic valve, thereby providing a device configured to treat the aortic valve and mitral valve simultaneously.

In another aspect, a method of reducing mitral valve regurgitation comprises delivering an expandable body into the left ventricular outflow tract, wherein the expandable body is configured to urge the anterior leaflet of a mitral valve toward the posterior leaflet of a mitral valve, thereby improving leaflet coaption. In one variation, the expandable body may comprise a stent configured to be delivered into the left ventricular outflow tract in a minimally invasive manner. The stent is preferably delivered to a location in the left ventricular outflow tract just beneath the aortic valve.

In another preferred embodiment, a tether or other tension member is provided for pulling the anterior leaflet toward the posterior leaflet. In one embodiment, the tether is located within the left ventricle. In another embodiment, the tether is located within the left atrium. The tether is configured to pull opposing regions of tissue into closer proximity for reshaping the mitral valve annulus.

In another aspect, a method for repairing a mitral valve involves providing a repair device having a deployment mechanism for independently applying first and second fastener elements to first and second regions of a mitral valve annulus. The repair device is used to grasp the first region of tissue with a vacuum force and then deploy a first fastener element into the first region of tissue. The first region of tissue is then disengaged from the repair device while leaving the first fastener element deployed therein. The repair device is then used to grasp the second region of tissue with a vacuum force and then deploy the second fastener element into the second region of tissue. The second region of tissue is then disengaged. The first and second fastener elements are then pulled together for reducing the distance between the first and second regions of tissue, thereby improving coaption of the mitral valve leaflets.

BRIEF DESCRIPTION OF THE DRAWINGS

FIG. 3 is a cross-sectional view generally illustrating one preferred medical implant configured for applying a force along the atrial septum.

FIG. 4 is a cross-sectional view generally illustrating another preferred medical implant configured for applying a force along the ventricular septum.

DETAILED DESCRIPTION

Various embodiments of the present invention depict medical implants and methods of use that are well-suited for treating mitral valve regurgitation. It should be appreciated that the principles and aspects of the embodiments disclosed and discussed herein are also applicable to other devices having different structures and functionalities. For example, certain structures and methods disclosed herein may also be applicable to the treatment of other heart valves or other body organs. Furthermore, certain embodiments may also be used in conjunction with other medical devices or other procedures not explicitly disclosed. However, the manner of adapting the embodiments described herein to various other devices and functionalities will become apparent to those of skill in the art in view of the description that follows.

Figure 1:
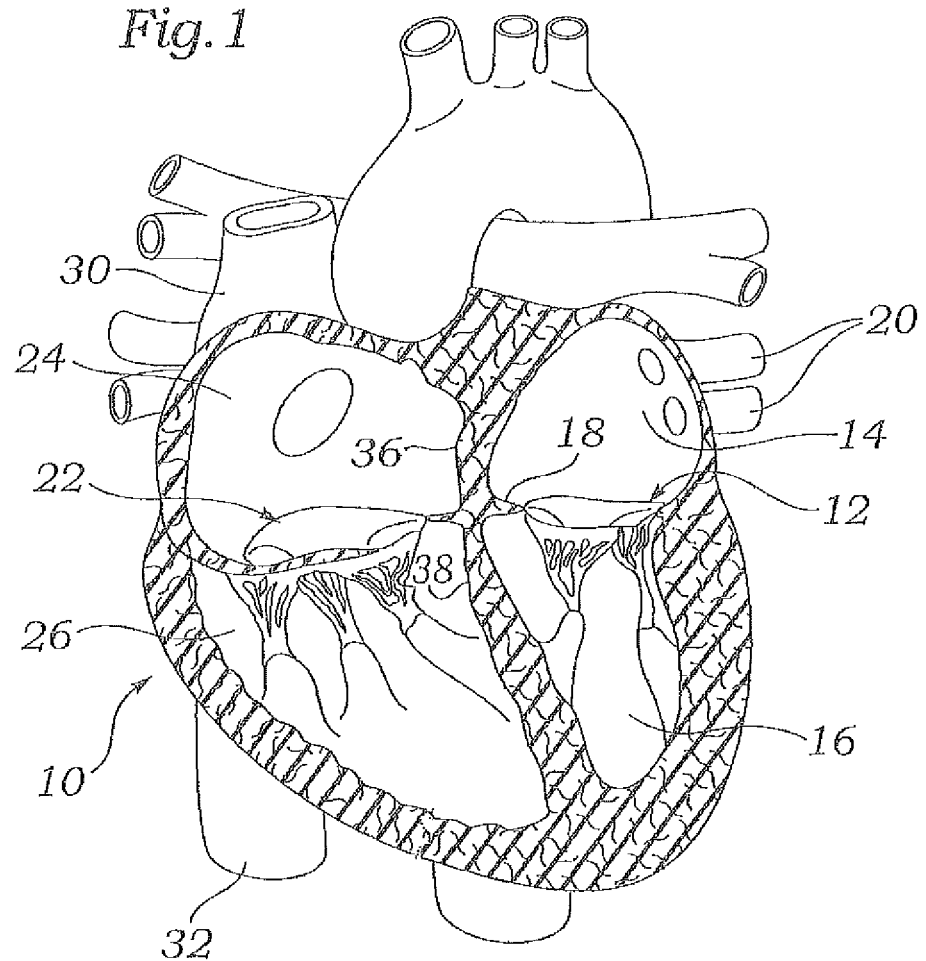
FIG. 1 is a first cross-sectional view of a typical four-chambered heart.

With reference now to FIG. 1, a four-chambered heart 10 is illustrated for background purposes. On the left side of the heart, the mitral valve 12 is located between the left atrium 14 and left ventricle 16. The mitral valve generally comprises two leaflets, an anterior leaflet and a posterior leaflet. The mitral valve leaflets are attached to a mitral valve annulus 18, which is defined as the portion of tissue surrounding the mitral valve orifice. The left atrium receives oxygenated blood from the pulmonary veins 20. The oxygenated blood that is collected in left atrium enters into the left ventricle through the mitral valve 12. Contraction of the left ventricle forces blood through the aortic valve and into the aorta.

On the right side of the heart, the tricuspid valve 22 is located between the right atrium 24 and right ventricle 26. The right atrium receives blood from the superior vena cava 30 and the inferior vena cava 32. The superior vena cava 30 returns de-oxygenated blood from the upper part of the body and the inferior vena cava 32 returns the de-oxygenated blood from the lower part of the body. The right atrium also receives blood from the heart muscle itself via the coronary sinus. The blood in the right atrium enters into the right ventricle through the tricuspid valve. Contraction of the right ventricle forces blood through the pulmonic valve and into the pulmonary trunk and then pulmonary arteries. The blood enters the lungs for oxygenation and is returned to the left atrium via the pulmonary veins 20.

The left and right sides of the heart are separated by a wall generally referred to as a septum. The portion of the septum that separates the two upper chambers (the right and left atria) of the heart is termed the atrial (or interatrial) septum 36 while the portion of the septum that lies between the two lower chambers (the right and left ventricles) of the heart is called the ventricular (or interventricular) septum 38.

On the left side of the heart, enlargement (i.e., dilation) of the mitral valve annulus 18 can lead to regurgitation (i.e., reversal of bloodflow) through the mitral valve 12. More particularly, when a posterior aspect of the mitral valve annulus 18 dilates, the posterior leaflet may be displaced from the anterior leaflet. As a result, the anterior and posterior leaflets fail to close completely and blood is capable of flowing backward through the resulting gap.

Figure 2:
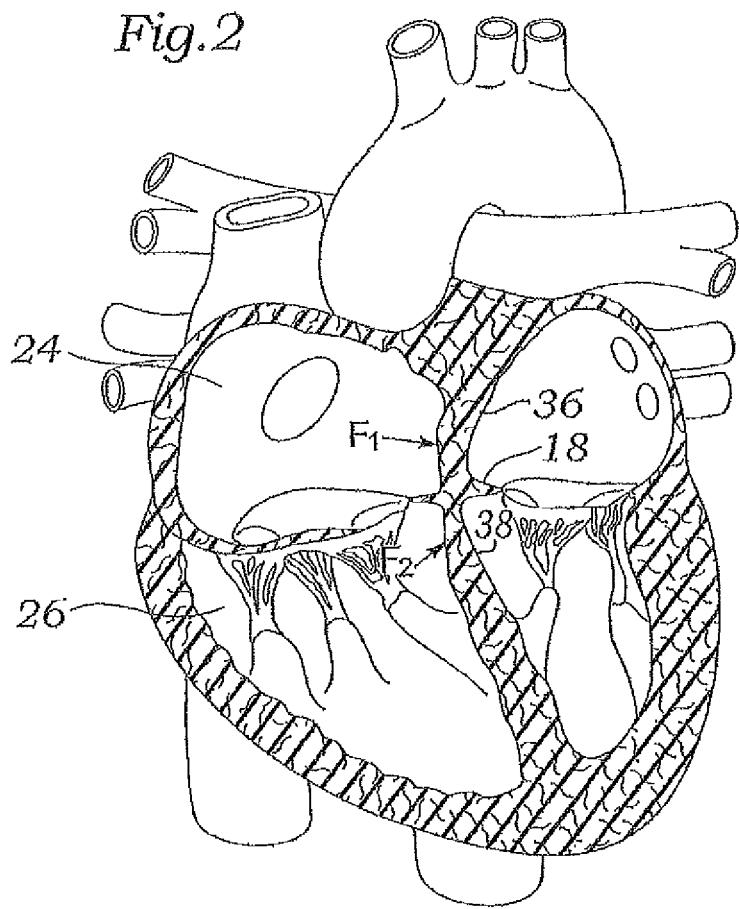
FIG. 2 is a cross-sectional view generally illustrating forces pushing against a septum for reshaping a mitral valve annulus.

With reference now to FIG. 2, according to one aspect of the invention, a lateral force $F_1$ may be applied to the atrial septum 36 from within the right atrium 24 for altering the geometry of the mitral valve annulus on the left side of the heart. More particularly, the force applied along the atrial septum 36 may be used to reshape the mitral valve annulus 18. The resulting change in shape causes the anterior leaflet of the mitral valve to be located closer to the posterior leaflet. The effect of this is to close the gap between the leaflets. By closing the gap, leaflet coaption is improved, thereby reducing or eliminating mitral valve regurgitation. In addition or alternatively, a force $F_2$ may be applied to the ventricular septum 38 from within the right ventricle 26 to reshape the mitral valve annulus in a similar manner. In either case, it is preferable that the force is applied to the septum at a location close to the mitral valve annulus.

Figure 3A:
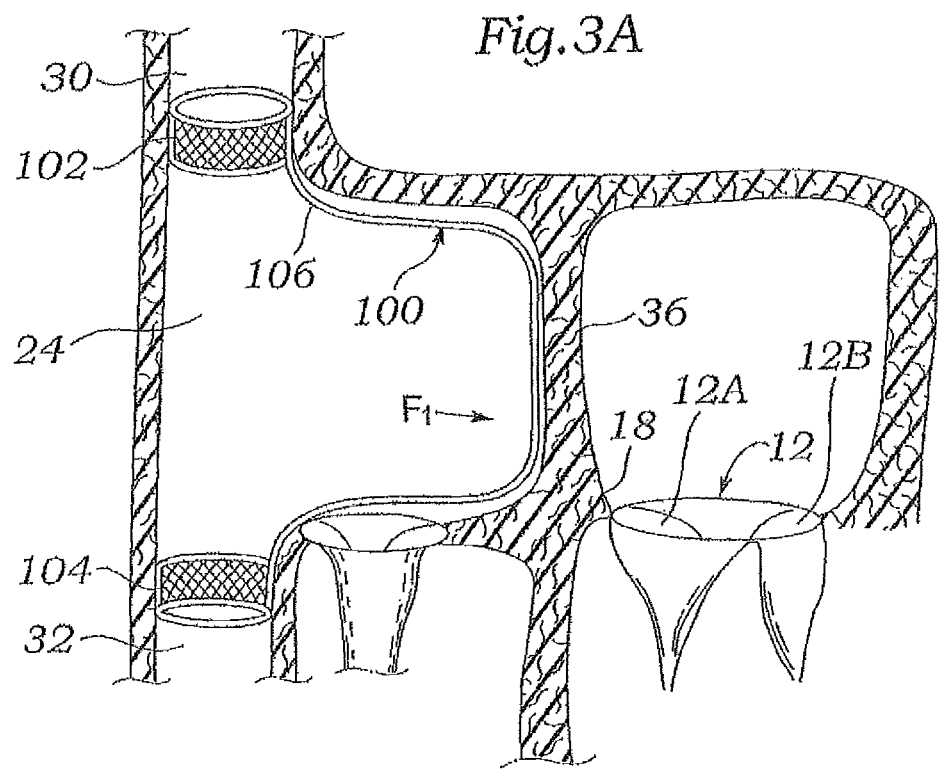
FIG. 3A is a schematic view illustrating the function of the implant of FIG. 3.
Figure 3B:
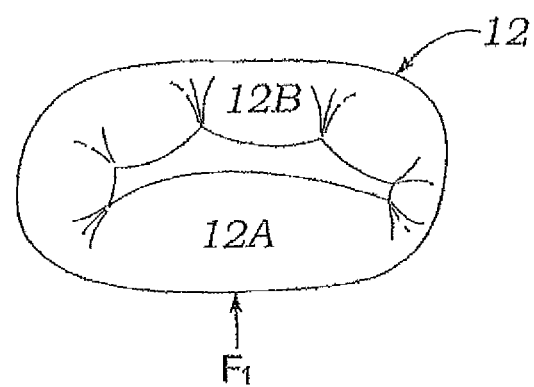
FIG. 3B illustrates the force acting on the anterior leaflet for urging the anterior leaflet toward the posterior leaflet.

With reference now to FIGS. 3 through 3B, one preferred embodiment of a mitral valve repair implant 100 is illustrated. The implant 100 is deployed substantially within the right atrium 24 and is configured to press against the atrial septum 36, preferably along a lower portion of the atrial septum. One preferred embodiment of the implant 100 comprises, generally, a first anchor 102, a second anchor 104 and a pusher member 106. The first anchor 102 is preferably an expandable stent configured to expand within the superior vena cava 30, preferably along or adjacent to the ostium wherein the superior vena cava empties into the right atrium. The second anchor 104 is preferably an expandable stent configured to expand in the inferior vena cava 32, preferably along or adjacent to the ostium wherein the inferior vena cava empties into the right atrium. The superior and inferior vena cava are desirable anchoring points because the tissue in this region is relatively stable and non-compliant and thereby provides a suitable foundation for anchoring the implant 100. Although the illustrated embodiment comprises two anchors, it will be appreciated that a device may be provided with only a single anchor while still remaining within the scope of the present invention.

The pusher member 106 preferably takes the form of an elongate bridge extending between the first and second anchors. The pusher member may comprise a curved or bow-shaped wire configured for contacting the atrial septum 36. The implant may be formed of any suitable biocompatible material. In one embodiment, the pusher member 106 is formed at least in part from a shape memory material that bows outward after deployment. As illustrated, the pusher member is preferably shaped to extend along a path within the right atrium (e.g., along the wall) that minimizes adverse hemodynamic effects.

The pusher member 106 is configured for pushing against the atrial septum after the implant 100 has been deployed. In one embodiment, a resorbable material may be used to hold the pusher member in a contracted position during delivery and deployment. However, over time, the material is resorbed such that the pusher member is allowed to lengthen, thereby causing the pusher member to bow outward.

Resorbable materials are those that, when implanted into a human body, are resorbed by the body by means of enzymatic degradation and also by active absorption by blood cells and tissue cells of the human body. Examples of such resorbable materials are PDS (Polydioxanon), Pronova (Poly-hexafluoropropylen-VDF), Maxon (Polyglyconat), Dexon (polyglycolic acid) and Vicryl (Polyglactin). As explained in more detail below, a resorbable material may be used in combination with a shape memory material, such as Nitinol, Elgiloy or spring steel to allow the superelastic material to return to a predetermined shape over a period of time.

In the illustrated embodiment, the first and second anchors 102, 104 are both generally cylindrically shaped members. The first and second anchors 102, 104 each have a compressed state and an expanded state. In the compressed state, each of the first and second anchors has a diameter that is less than the diameter of the superior and inferior vena cava, respectively. In the expanded state, each of the first and second anchors has a diameter that is preferably about equal to or greater than the diameter of the section of vena cava to which each anchor will be aligned. The anchors are preferably made from tubes of shape memory material, such as, for example, Nitinol. However, the anchors 102, 104 may also be made from any other suitable material, such as stainless steel. When the anchors are formed with stainless steel, the anchors may be deployed using a balloon catheter as known in the art. Although the anchor mechanisms take the form of stents for purposes of illustration, it will be appreciated that a wide variety of anchoring mechanisms may be used while remaining within the scope of the invention.

With particular reference to FIG. 3A, the functionality of the implant is schematically illustrated. It can be seen that the implant 100 is deployed in the right atrium 24 with the first anchor 102 expanded in the superior vena cava 30 and the second anchor 104 deployed in the inferior vena cava 32. The pusher member 106 extends between the anchors and is shaped for pressing against the atrial septum 36 for reshaping the mitral valve annulus 18 on the left side of the heart. In other words, the implant 100 applies a force $F_1$ against the atrial septum. With reference to FIGS. 3A and 3B, it can be seen that the force $F_1$ is transferred through the atrial septum for pushing the anterior leaflet 12A of the mitral valve 12 toward the posterior leaflet 12B.

With reference now to FIG. 4, an alternative device 200 is illustrated for reshaping a mitral valve annulus. In this embodiment, the implant 200 is configured for deployment within the right ventricle 26. In one preferred embodiment, the device generally comprises a U-shaped member 202 that is suitable for deployment in or adjacent to the tricuspid valve 22. More particularly, the U-shaped member may extend around the chordae and/or papillary muscles of the tricuspid valve. In a manner substantially similar to that described above, the U-shaped member urges the ventricular septum outward for reshaping the mitral valve annulus 18 and pushing the anterior leaflet of the mitral valve toward the posterior leaflet. Although a U-shaped member is shown for purposes of illustration, any suitable force applying member may be used.

Although particular devices have been illustrated for purposes of discussion, it will be appreciated that a variety of alternative mechanisms may be used to apply a force along the septum for reshaping the mitral valve annulus. For example, in one alternative embodiment, an expandable cage may be deployed in the right atrium for urging the atrial septum toward the left side of the heart, thereby moving the anterior leaflet toward the posterior leaflet. Still further, it will be appreciated that the devices and methods described herein may also be used to treat the tricuspid valve. Those skilled in the art will appreciate that a substantially similar device may be deployed in the left atrium (or left ventricle) for pushing the septum toward the right side of the heart and improving coaption of the tricuspid leaflets.

To further enhance the ability to reshape the mitral valve annulus, an implant for pushing against the anterior leaflet of the mitral valve, such as the embodiments described above, may be used in combination with an implant deployed in the coronary sinus for pushing against the posterior leaflet of the mitral valve. One example of a device configured for deployment in the coronary sinus is described in Applicant's co-pending application Ser. No. 11/238,853, filed Sep. 28, 2005, the contents of which are hereby incorporated by reference. It will be recognized that, by applying compressive forces to both the anterior and posterior sides of the mitral valve, the ability to improve leaflet coaption is further enhanced.

Figure 5:
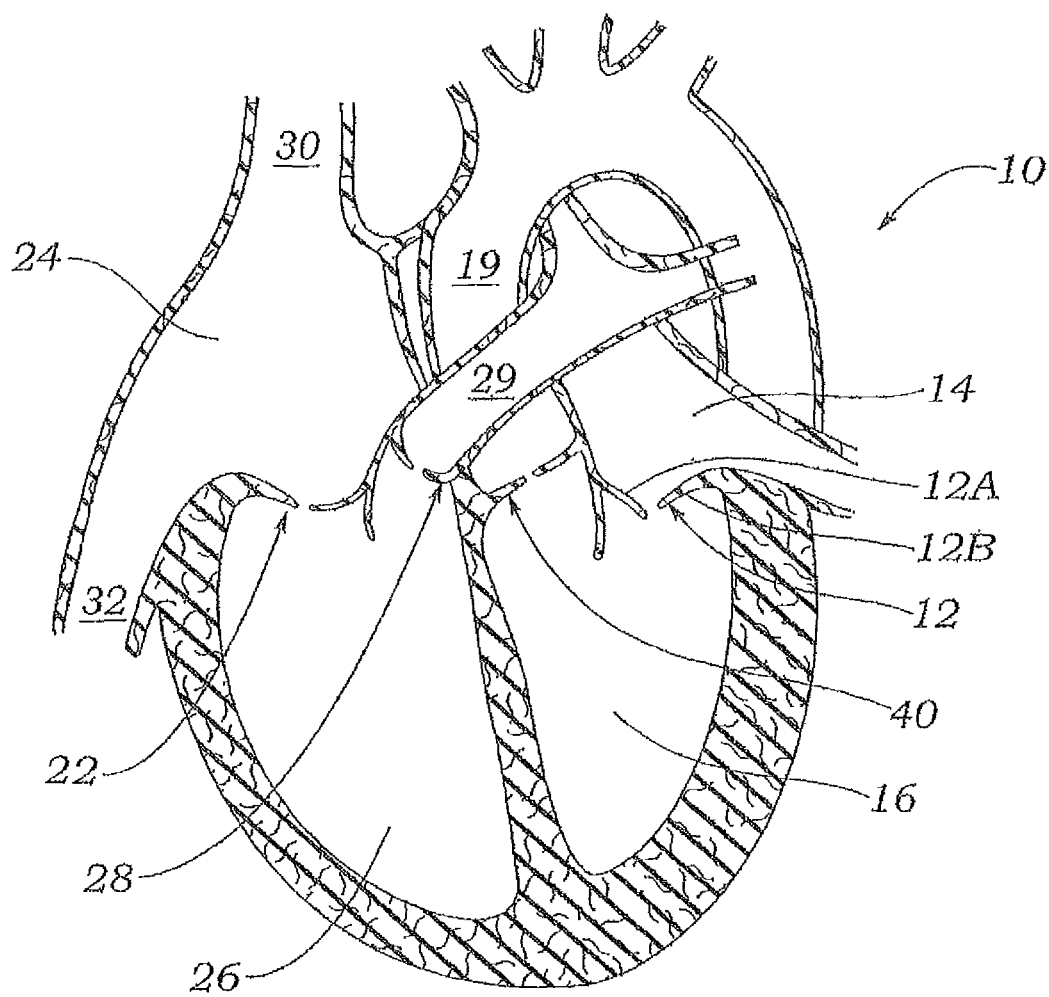
FIG. 5 is a second cross-sectional view of a typical four-chambered heart.

With reference now to FIG. 5, an alternative illustration of a four-chambered heart 10 is provided wherein all four heart valves can be seen. As discussed above, on the left side of the heart, the mitral valve 12 is located between the left atrium 14 and left ventricle 16. The mitral valve generally comprises two leaflets, an anterior leaflet 12A and a posterior leaflet 12B. Contraction of the left ventricle forces blood through the left ventricular outflow tract (LVOT) and into the aorta 19. The aortic valve 40 is located between the left ventricle 16 and the aorta 19 for ensuring that blood flows in only one direction (i.e., from the left ventricle to the aorta). As used herein, the term left ventricular outflow tract, or LVOT, is intended to generally include the portion of the heart through which blood is channeled from the left ventricle to the aorta. The LVOT shall include the aortic valve annulus and the adjacent region extending below the aortic valve annulus. For purposes of this discussion, the LVOT shall also include the portion of the ascending aorta adjacent to the aortic valve.

On the right side of the heart, the tricuspid valve 22 is located between the right atrium 24 and right ventricle 26. The right atrium receives blood from the superior vena cava 30 and the inferior vena cava 32. Contraction of the right ventricle forces blood through the right ventricular outflow tract (RVOT) and into the pulmonary arteries. The pulmonic valve 28 is located between the right ventricle and the pulmonary trunk 29 for ensuring that blood flows in only one direction from the right ventricle to the pulmonary trunk. As used herein, the term right ventricular outflow tract, or RVOT, generally includes the pulmonary valve annulus and the adjacent region extending below the pulmonary valve annulus.

Figure 6:
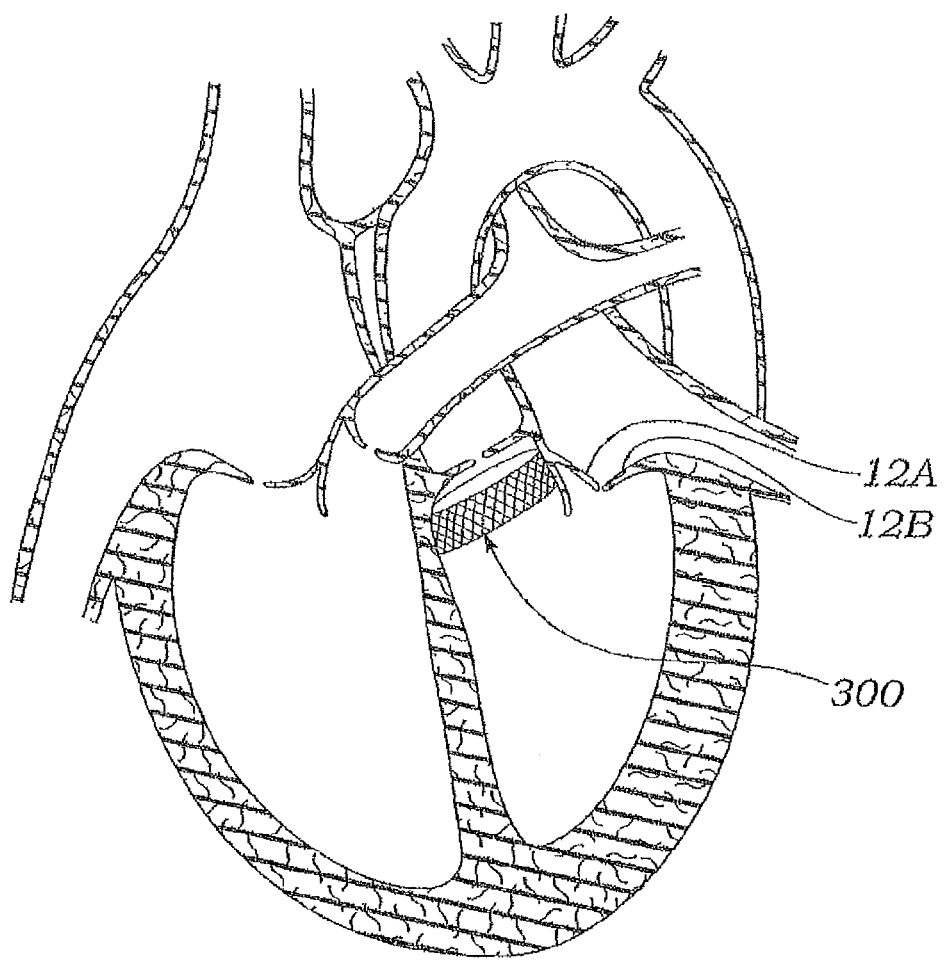
FIG. 6 illustrates an expandable stent deployed in the left ventricular outflow tract for reshaping the mitral valve annulus.

With reference now to FIG. 6, another preferred embodiment of a medical implant 300 is illustrated for treating mitral valve regurgitation. In this embodiment, the implant 300 is configured for deployment within the LVOT at a location beneath the aortic valve. Due to the proximity of the LVOT with respect to the anterior portion of the mitral valve annulus, it has been found that the deployment of an implant within the LVOT may be used to reshape the mitral valve annulus and thereby affect the position of the anterior leaflet of the mitral valve. More particularly, the implant is configured to apply a force which pushes the anterior leaflet 12A toward the posterior leaflet 12B for improving leaflet coaption in the mitral valve.

Figure 6A:
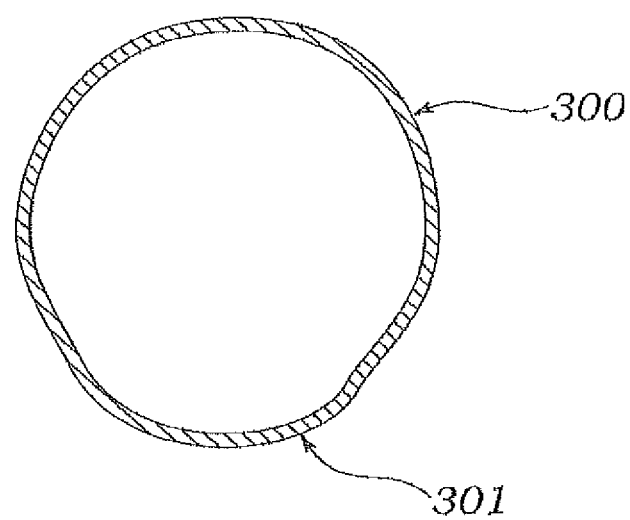
FIG. 6A illustrates a preferred cross-section of an expandable stent having a protrusion configured to apply a force along the anterior portion of the mitral valve annulus.

In one preferred embodiment, the implantable device 300 generally comprises an expandable stent. The stent may be self-expanding or balloon-expandable. When a self-expanding stent is used, the stent is preferably formed of a shape memory material and may be delivered using a sheath. After reaching the treatment site, the stent is emitted from the sheath and is allowed to self expand. When a balloon-expandable stent is used, the stent is preferably formed of stainless steel. The stent is crimped and placed over a deflated balloon provided on the distal end portion of an elongate catheter. The distal end portion of the catheter is advanced to the treatment site and the balloon is inflated for expanding the stent within the LVOT. If desired, the stent may further comprise engagement members, such as, for example, barbs or hooks, to enhance the securement of the stent at the treatment site. As shown in FIG. 6A, if desired, the stent may be formed with a bulge or protrusion 301 for increasing the force applied in the region of the anterior leaflet.

The implant 300 is preferably delivered to the treatment site using a minimally invasive procedure. In one preferred method of use, the device is inserted through the femoral artery and is advanced around the aortic arch to the treatment site. In another preferred method of use, the device is inserted into the femoral vein and is advanced from the right side of the heart to the left side of the heart via a trans-septal procedure. After reaching the left side of the heart, the device can be deployed within the LVOT.

The implant 300 is preferably configured to expand to a diameter greater than the natural diameter of the LVOT. As a result of the expansion, an outward force is applied along the LVOT. More particularly, a force is applied along a region of tissue adjacent the anterior portion of the mitral valve. The force urges the anterior leaflet toward the posterior leaflet of the mitral valve for reducing or eliminating mitral valve regurgitation.

The device may be used alone or in combination with another therapeutic device, such as an implant configured for deployment within the coronary sinus. When used with an implant in the coronary sinus, compressive forces may be applied along both the anterior and posterior portions of the mitral valve, thereby providing the clinician with an enhanced ability to improve leaflet coaption and reduce mitral valve regurgitation.

Figure 7:
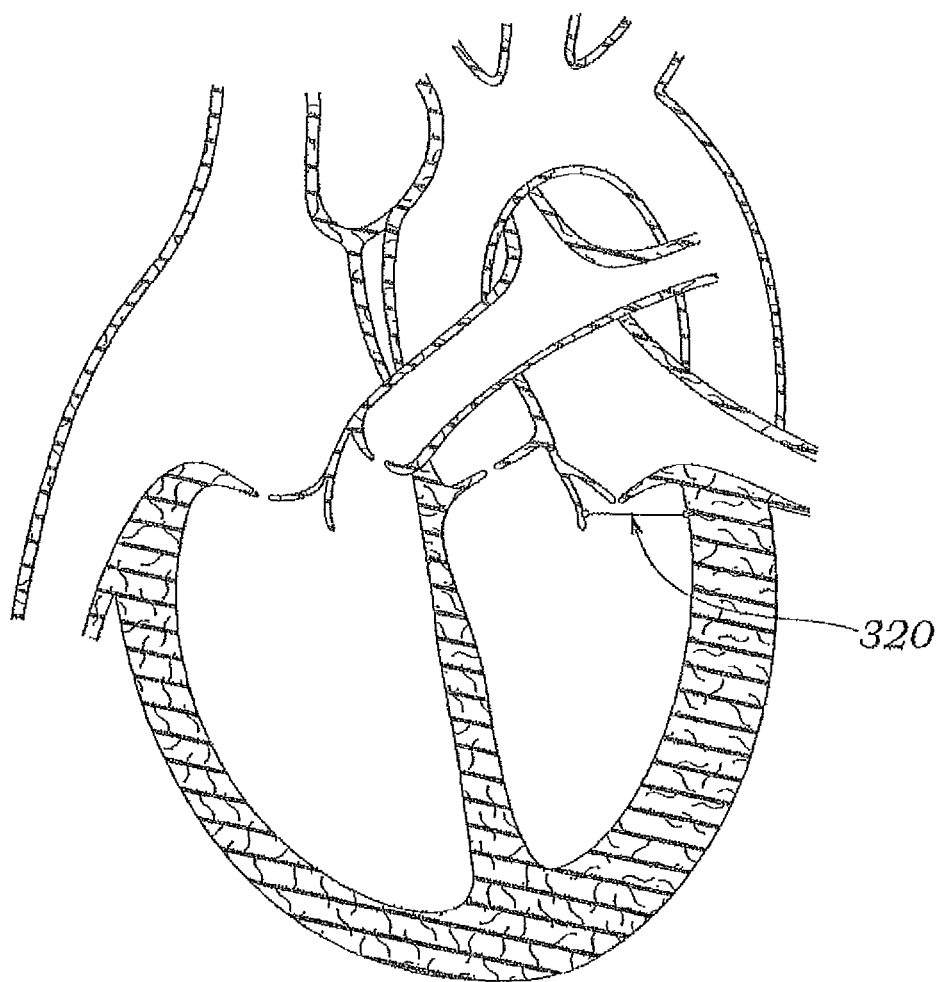
FIG. 7 illustrates yet another approach for treating a mitral valve wherein a tether extends across the left ventricle at a location beneath the mitral valve for improving mitral valve function.

With reference to FIG. 7, yet another device and method for treating mitral valve regurgitation is schematically illustrated. In this embodiment, a tether 320 or other tension member extends across a portion of the left ventricle for pulling the anterior and posterior mitral valve leaflets together. The tether may take the form of a suture which is passed through tissue along the walls of the left ventricle. One preferred device for deploying a suture or tether can be found in Applicant's co-pending application Ser. No. 10/389,721, filed Mar. 14, 2003, now published as U.S. Publication No. 2004/0181238, the contents of which are hereby incorporated by reference. In an alternative device, the tether may have barbs or other anchoring means for engaging the tissue. If necessary, more than one tether may be used for reshaping the mitral valve annulus and improving leaflet coaption.

Figure 8:
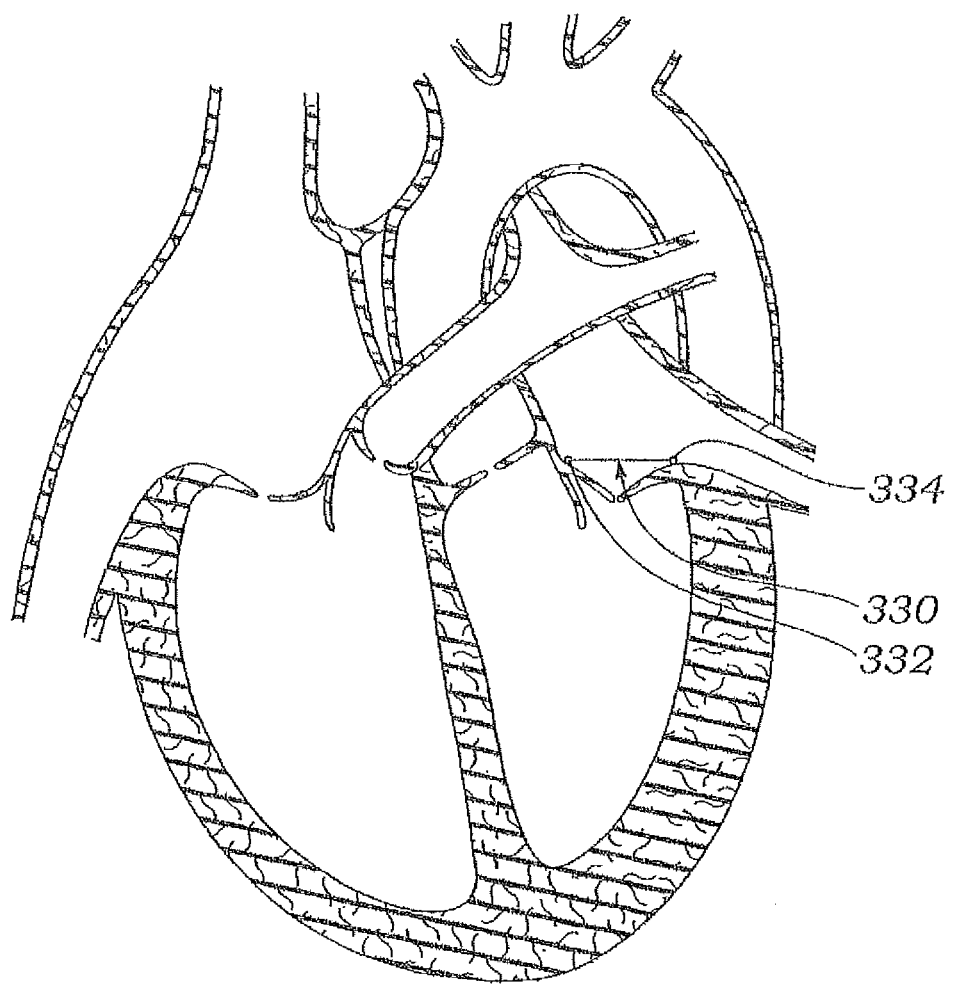
FIG. 8 illustrates a tether attached to opposing regions of a mitral valve annulus at a location above the mitral valve for improving mitral valve function.

With reference to FIG. 8, yet another alternative approach is schematically illustrated for treating the mitral valve. In this embodiment, a tether 330 or other elongate tension member extends across a portion of the left atrium for pulling the anterior and posterior mitral valve leaflets together. The tether is preferably attached to opposing regions of tissue on the mitral valve annulus. The tether may take the form of a suture which is tied or otherwise fastened to the tissue along the mitral valve annulus.

In one method of delivering the tether, a repair device is provided which has a deployment mechanism for applying first and second fastener elements to first and second regions of the mitral valve annulus. The first region of tissue is grasped using the repair device and the first fastener element 332 is deployed into the first region of tissue. The first region of tissue is disengaged from the repair device while leaving the first fastener element deployed therein. The second region of tissue is then grasped using the repair device and the second fastener element 334 is deployed into the second region of tissue. The second region of tissue is disengaged from the repair device while leaving the second fastener element deployed therein. The first and second fastener elements are attached by the tether 330. The tether pulls the first and second fastener elements together for reducing the distance between the first and second regions of tissue, thereby reshaping the mitral valve annulus. The tether is held in tension for maintaining the mitral valve annulus in the reshaped condition.

Figure 8A:
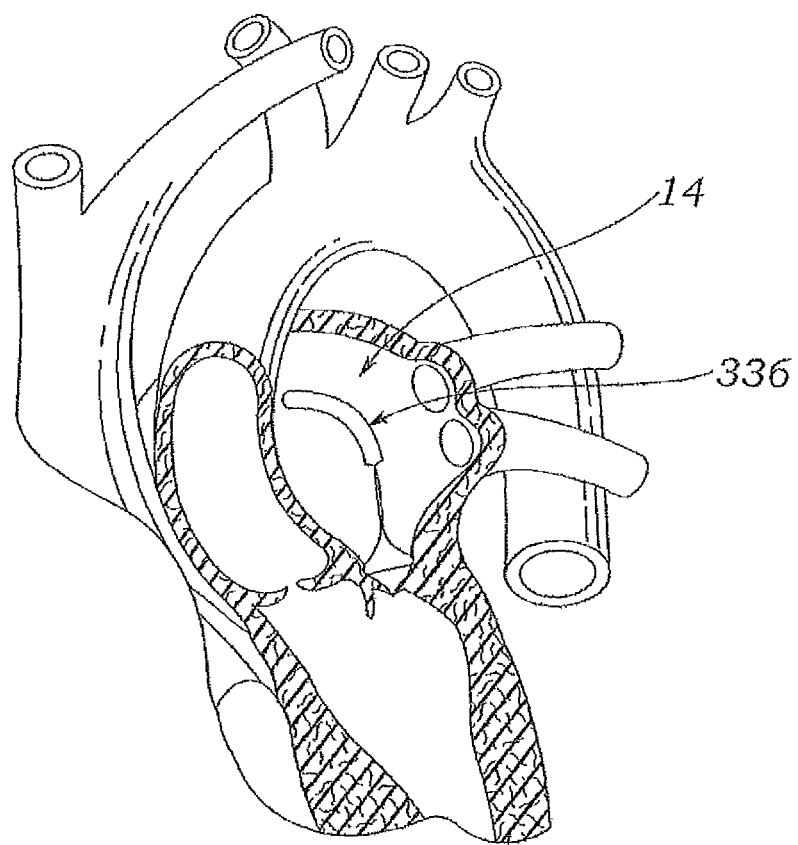
FIGS. 8A and 8B illustrate a preferred method of attaching a tether to the mitral valve annulus.
Figure 8B:
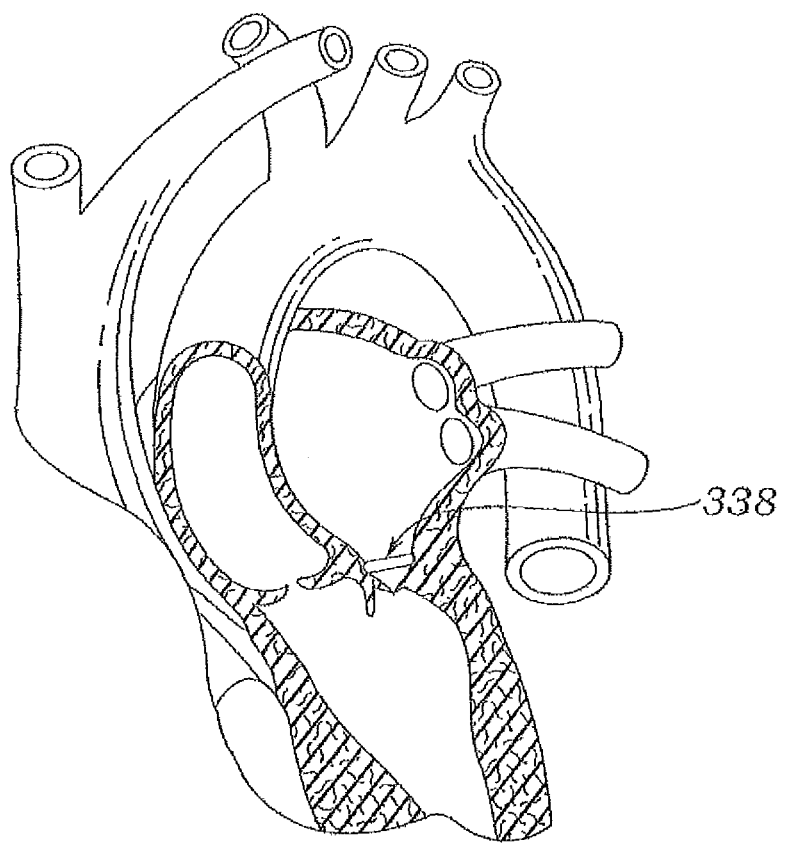

With reference to FIG. 8A, a more particular method of use will be described in more detail. In this method, a distal end portion of a therapy catheter 336 is percutaneously advanced into the left atrium 14. The therapy catheter preferably includes a side vacuum port (not shown) for grasping tissue. After grasping the tissue on one side of the mitral valve annulus, a needle is advanced from the catheter and through the tissue for advancing a first piece of suture through the tissue. The tissue is then released and the procedure is repeated on the other side of the annulus, thus creating a suture loop. As best shown in FIG. 8B, a clip or other fastener 338 is then advanced over the suture to hold the loop tight and the remaining suture is cut away and removed. The suture loop and clip provide the tether for maintaining the mitral valve annulus in the reshaped condition.

Figure 8C:
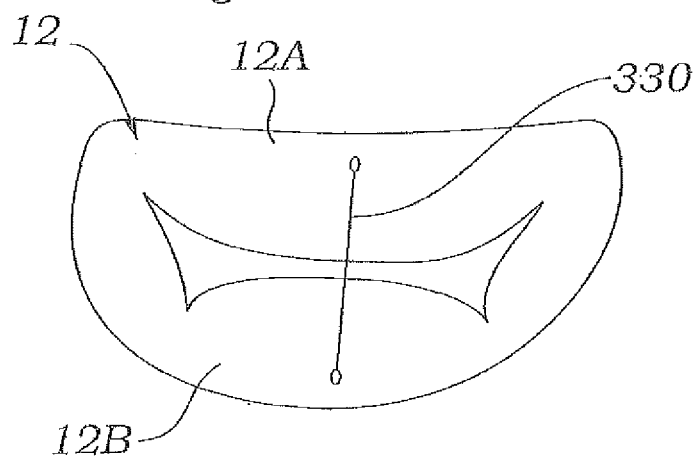
FIGS. 8C through 8E illustrate various tether configurations for reshaping the mitral valve annulus.
Figure 8D:
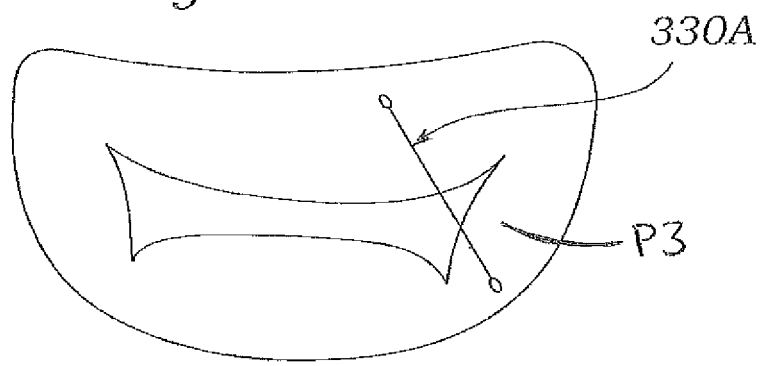
Figure 8E:
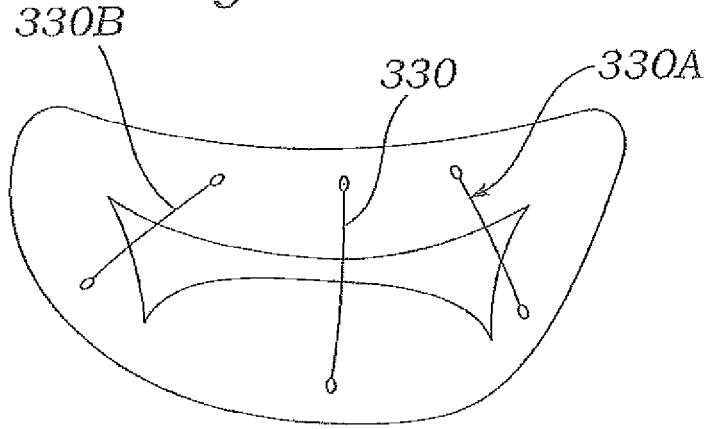

With reference to FIG. 8C, a mitral valve 12 is illustrated wherein a tether 330 has been secured to opposite sides of the mitral valve annulus along a central region of the mitral valve. The tether is attached with sufficient tension such that the mitral valve annulus is reshaped for improving coaption between the anterior leaflet 12A and posterior leaflet 12B. FIG. 8D illustrates an alternative approach wherein a tether 330A is secured to the posterior portion of the mitral valve annulus adjacent to a P3 scallop. FIG. 8E illustrates another alternative configuration wherein a plurality of tethers 330, 330A, 330B are provided. These various approaches are provided for purposes of illustration; however, it will be appreciated that a variety of alternative approaches may also be selected for treating a particular defect.

Figure 9:
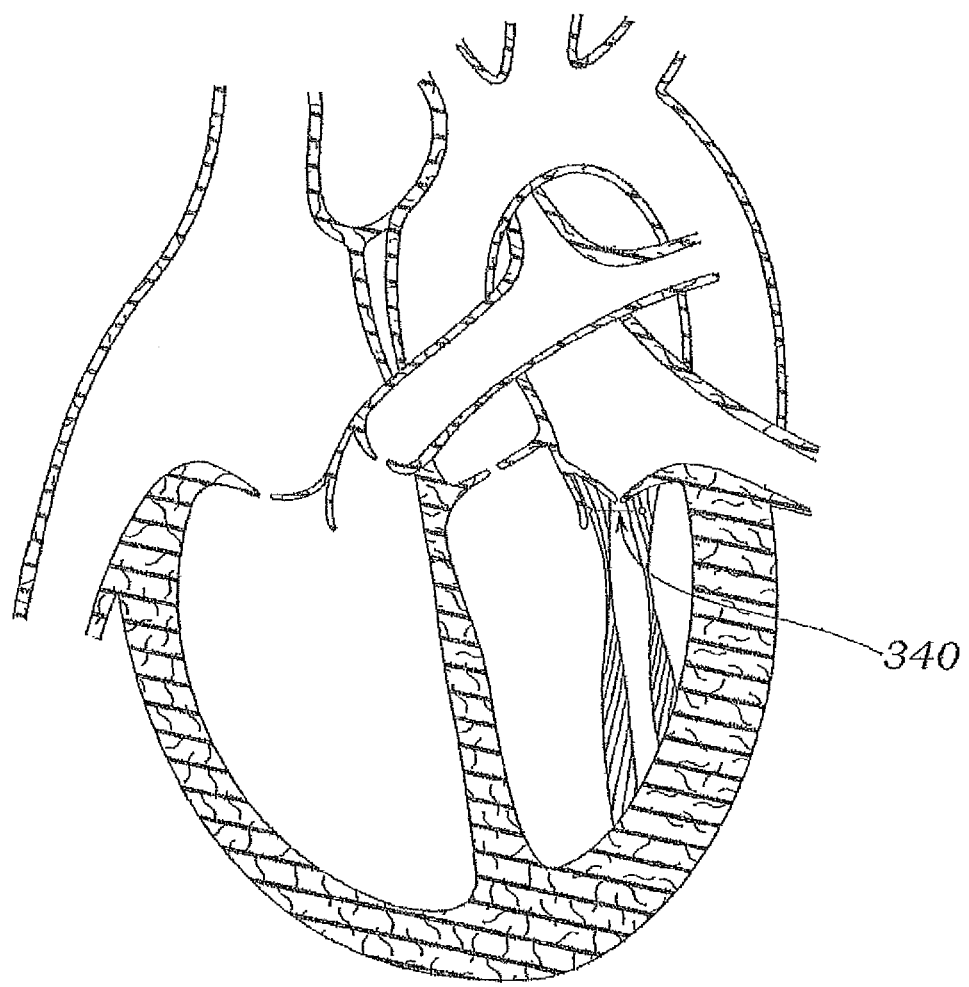
FIG. 9 illustrates an alternative approach wherein one end of a tether is attached to chordae within the left ventricle.

With reference to FIG. 9, another embodiment of a tether 340 is illustrated wherein at least one end of the tether is configured for attachment to chordae.

Figure 10:
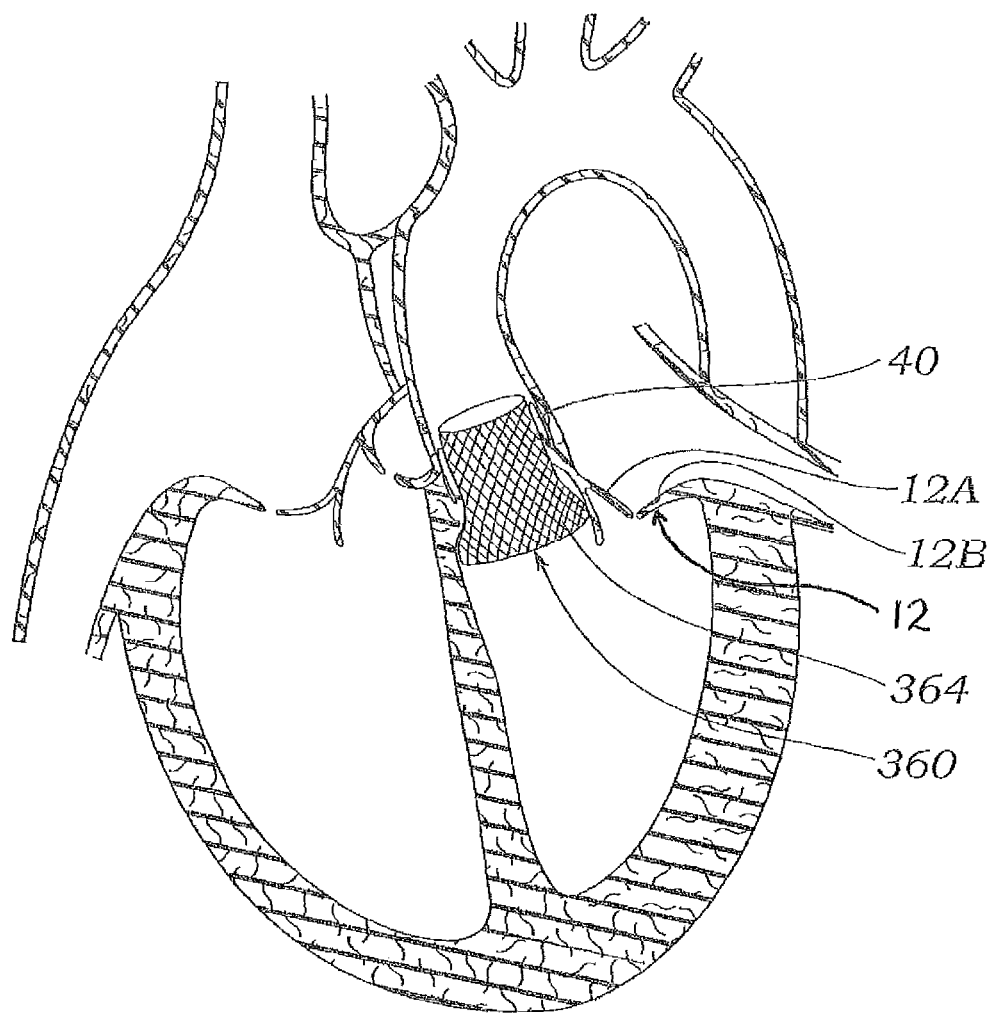
FIG. 10 illustrates a prosthetic valve for replacing a native aortic valve and including a lower portion configured for reshaping the mitral valve annulus.

With reference to FIG. 10, yet another approach for treating mitral valve regurgitation comprises a prosthetic valve 360 configured for deployment within the aortic valve annulus. The prosthetic valve preferably includes an expandable stent portion and a valvular structure disposed within the stent portion. The prosthetic valve is configured to replace the function of the native aortic valve 40. The stent portion of the prosthetic valve is configured to extend below the aortic valve annulus and into the LVOT. The stent is shaped to apply a force along the region of tissue which separates the LVOT from the mitral valve. The force moves the anterior leaflet 12A of the mitral valve 12 toward the posterior leaflet 12B for improving leaflet coaption. In a preferred configuration, the stent portion includes a generally tubular upper section which contains the valvular structure. If desired, the stent portion may include a flared lower portion 364 configured to engage and push against the tissue of the LVOT, thereby more effectively altering the position of the anterior leaflet 12A. This embodiment advantageously provides the clinician with the ability to treat both the aortic valve and the mitral valve with a single device. Addition details regarding the structure and use of prosthetic valves can be found in Applicant's U.S. Pat. No. 6,730,118, the contents of which are hereby incorporated by reference.

Figure 11:
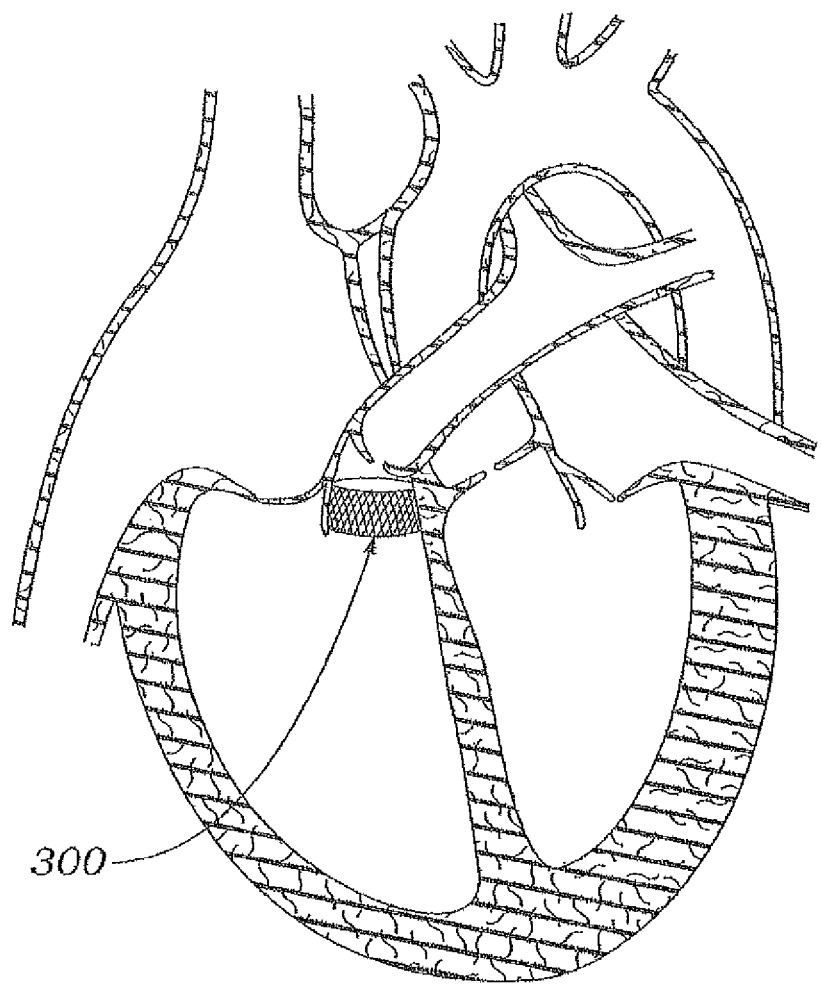
FIG. 11 illustrates a stent deployed in the right ventricular outflow tract for improving tricuspid valve function.

It will be recognized that the embodiments described above may also be used to treat a triscuspid valve in substantially similar manner. For example, with reference to FIG. 11, in an approach similar to that described with respect to FIG. 6, an expandable stent 300 may be deployed in the RVOT for pushing against the anterior region of the tricuspid valve. Depending on the particular anatomy, this method may be used to advantageously treat tricuspid valve regurgitation. Furthermore, aspects of each of the other embodiments described herein may also be used to treat the triscuspid valve.

Exemplary embodiments of the invention have been described, but the invention is not limited to these embodiments. Various modifications may be made within the scope without departing from the subject matter of the invention read on the appended claims, the description of the invention, and the accompanying drawings.

What is claimed is:

1. A method for reducing tricuspid valve regurgitation, the method comprising:
   radially expanding a radially-collapsed stent at a location below a native pulmonary valve such that the entire stent is positioned in a right ventricular outflow tract; and
   fixing the stent within the right ventricular outflow tract, the stent positioned adjacent to a native tricuspid valve, wherein after fixing the stent within the right ventricular outflow tract, an expanded diameter of the stent is larger than an inner diameter of the right ventricular outflow tract, the expanded stent pushing against an anterior region of the tricuspid valve, thereby improving coaption of leaflets of the tricuspid valve.

2. The method of claim 1, further comprising radially collapsing the stent to a reduced diameter.

3. The method of claim 2, further comprising coupling the radially-collapsed stent to a distal end portion of an elongate catheter.

4. The method of claim 3, further comprising advancing the distal end portion of the elongate catheter through a patient's vasculature and delivering the stent into the right ventricular outflow tract.

5. The method of claim 4, wherein advancing the distal end portion of the elongate catheter through a patient's vasculature comprises advancing the distal end portion of the elongate catheter through a femoral vein.

6. The method of claim 1, wherein the stent comprises a protrusion along a side of the expanded stent, the protrusion positioned to push against the anterior region of the tricuspid valve after fixing the stent within the right ventricular outflow tract.

7. The method of claim 1, wherein the stent includes an unobstructed lumen extending longitudinally therethrough.

8. The method of claim 1, wherein the stent is self-expanding.

9. The method of claim 1, wherein radially expanding the radially-collapsed stent comprises expanding the radially collapsed stent using a balloon.

10. A method for reducing tricuspid valve regurgitation, the method comprising:
    radially collapsing a stent to a reduced diameter;
    coupling the radially-collapsed stent to a distal end portion of an elongate catheter;
    advancing the distal end portion of the elongate catheter through a patient's vasculature and delivering the stent into a right ventricular outflow tract;

radially expanding the radially-collapsed stent at a location below a native pulmonary valve such that the entire stent is positioned in the right ventricular outflow tract; and fixing the stent within the right ventricular outflow tract, the stent positioned adjacent to a native tricuspid valve, wherein after fixing the stent within the right ventricular outflow tract, an expanded diameter of the stent is larger than an inner diameter of the right ventricular outflow tract, and wherein the stent comprises a protrusion along a side of the expanded stent, the protrusion of the expanded stent positioned to push against an anterior region of the tricuspid valve, thereby improving coaption of leaflets of the tricuspid valve.

11. The method of claim 1, wherein the stent includes an unobstructed lumen extending longitudinally therethrough.

12. The method of claim 1, wherein the stent is self-expanding.

13. The method of claim 1, wherein radially expanding the radially-collapsed stent comprises expanding the radially-collapsed stent using a balloon.

* * * * *